United States Patent
Wohlrab et al.

(10) Patent No.: US 6,689,349 B1
(45) Date of Patent: Feb. 10, 2004

(54) SKIN PROTECTION AGENTS CONTAINING A FRAGMENT MIXTURE PRODUCED FROM HYALURONIC ACID BY HYDROLYSIS

(75) Inventors: Wolfgang Wohlrab, Halle (DE); Reinhard Neubert, Halle (DE); Christoph Huschka, Halle (DE); Peter-Jürgen Müller, Jena (DE); Jörg-Herman Ozegowski, Jena (DE); Dieter Koegst, Osterweddingen (DE); Gerhard Fries, Osterweddingen (DE)

(73) Assignee: esparma GmbH, Osterweddingen (DE)

( * ) Notice: Subject to any disclaimer, the term of this patent is extended or adjusted under 35 U.S.C. 154(b) by 0 days.

(21) Appl. No.: 09/868,955

(22) PCT Filed: Dec. 22, 1999

(86) PCT No.: PCT/EP99/10336
§ 371 (c)(1),
(2), (4) Date: Jun. 22, 2001

(87) PCT Pub. No.: WO00/38647
PCT Pub. Date: Jul. 6, 2000

(30) Foreign Application Priority Data

Dec. 23, 1998 (DE) ......................... 198 60 544

(51) Int. Cl.[7] ............. A61K 7/09; A61K 7/075; A61K 6/00; A61K 9/127; A61K 7/16; A01N 43/04

(52) U.S. Cl. ............ 424/78.02; 424/401; 424/450; 424/59; 424/78.03; 514/54; 514/844; 514/937; 514/938

(58) Field of Search ............ 424/400, 401, 424/450, 59, 78.02, 78.03, 94.6, 520, 94.62; 514/844, 937, 938, 946, 947, 54

(56) References Cited

U.S. PATENT DOCUMENTS 4,303,676 A 12/1981 Balazs
5,571,503 A 11/1996 Mausner (List continued on next page.)

FOREIGN PATENT DOCUMENTS

DE 197 23 308 A1 12/1998
EP 0295092 * 12/1988

(List continued on next page.)

OTHER PUBLICATIONS

International Search Report for PCT/EP99/10336 mailed Apr. 25, 2000.
Greiling et al. "On the Heterogeneity of Hyaluronate Lyase" Z. Physiol Chem., vol. 340 (1965).

(List continued on next page.)

Primary Examiner—Michael G. Hartley
Assistant Examiner—Sharmila S Gollamudi
(74) Attorney, Agent, or Firm—Leydig Voit & Mayer, Ltd.

(57) ABSTRACT

The invention relates to an agent for the treatment, prophylaxis and metaphylaxis of functional and structural disorders of the skin caused by external factors. The agent contains a hyaluronic acid partially digested with a microbiological hyaluronate lyase. The hyaluronic acid fragment mixture is incorporated in different galenic formulations to which other hydrophilic and/or lipophilic active substances and/or auxiliary substances can be added. Fields of application of the invention in human and veterinary medicine relate to the treatment and/or the prophylaxis of skin damage caused by environmental factors including UV, dry skin conditions and skin ageing.

17 Claims, 11 Drawing Sheets

DNA-synthesis performance of HaCaT keratinocytes under the influence of hyaluronic acid fragments with an average molar mass of 223000 g /mol
Incubation period 24 h

U.S. PATENT DOCUMENTS 5,852,002 A * 12/1998 Falk et al. .................... 514/54
5,866,142 A *  2/1999 Riordan ...................... 424/401

FOREIGN PATENT DOCUMENTS

| FR | 2 448 903 A | 10/1980 |
| GB | 1060513 | 3/1967 |
| GB | 1179787 | 1/1970 |
| JP | 62-104579 A | 5/1987 |
| JP | 9-98739 A | 4/1997 |
| JP | 11-124401 A | 5/1999 |
| KR | 9400998 B1 | 2/1994 |

OTHER PUBLICATIONS

Galikeev, Kh. L. "The Role of Hyaluronidase of Streptococci in the Mechanism of Corpuscula Antigen Resorption and it's Penetration Through the Mucous Barrier of Respiratory Tracts" *Z. Mikrobiol., Epidemiol., Immunobiol.*, 44 (3), 60–3 (1967).

Jedrzejas et al. "Expression and Purification of Streptococcus Pneumoniae Hyaluronate Lyase from *Escherichia coli*" *Protein Expression and Purification*, 13 (1), 83–9 (Jun. 1998).

* cited by examiner

Figure 1　DNA-synthesis performance of HaCaT keratinocytes under the influence of hyaluronic acid fragments with an average molar mass of 223000 g /mol
Incubation period 24 h Figure 2  DNA-synthesis performance of HaCaT keratinocytes under the influence of hyaluronic acid fragments with an average molar mass of 338000 g/ mol
Incubation period 24 h Figure 3  DNA-synthesis performance of HaCaT keratinocytes under the influence of hyaluronic acid fragments with an average molar mass of 349000 g/mol Incubation period 24 h Figure 4    DNA-synthesis performance of HaCaT keratinocytes under the influence of hyaluronic acid fragments with an average molar mass of 600700 g/ mol Incubation period 24 h Figure 5  DNA-synthesis performance of HaCaT keratinocytes under the influence of hyaluronic acid with an average molar mass of 1,001,000 g/mol
Incubation period 24 h Figure 6  Determination of the number of living cells 24 h after UV-B irradiation (120mJ/cm$^2$) by means of vital staining with prior incubation with hyaluronic acid fragments having an average molar mass of 223000 g/mol for 1 h, 24 h, 48 h or 72 h (*=significant to the irradiated control, $p < 0.01$, n=24)

Figure 7   Determination of the number of living cells 24 h after UV-B irradiation (120mJ/cm$^2$) by means of vital staining with prior incubation with hyaluronic acid fragments having an average molar mass of 338000 g/mol for 1 h, 24 h, 48 h or 72 h
(*=significant to the irradiated control, $p < 0.01$, $n = 24$)

Figure 8   Determination of the number of living cells 24 h after UV-B irradiation (120mJ/cm$^2$) by means of vital staining with prior incubation with hyaluronic acid fragments having an average molar mass of 349000 g/mol for 1 h, 24 h, 48 h or 72 h
(*=significant to the irradiated control, p <0.01, n=24)

Figure 9   Determination of the number of living cells 24 h after UV-B irradiation (120mJ/cm$^2$) by means of vital staining with prior incubation with hyaluronic acid fragments having an average molar mass of 600700g/mol for 1 h, 24 h, 48 h or 72 h (*=significant to the irradiated control, p <0.01, n=24)

Figure 10   Determination of the number of living cells 24 h after UV-B irradiation (120mJ/cm$^2$) by means of vital staining with prior incubation with hyaluronic acid fragments having an average molar mass of 1001000g/mol for 1 h, 24 h, 48 h or 72 h
(*=significant to the irradiated control, p <0.01, n=24)

Figure 11   Absorption spectrum of the hyaluronic acid fragments of the mean molecule size of 223000 g/mol

SKIN PROTECTION AGENTS CONTAINING A FRAGMENT MIXTURE PRODUCED FROM HYALURONIC ACID BY HYDROLYSIS

The invention relates to agents or galenic formulations for the treatment, prophylaxis and metaphylaxis of functional disorders of the skin as a result of external influences and/or as a result of other diseases. It has its preferred fields of application in human and veterinary medicine in the treatment, prophylaxis or metaphylaxis of skin damage caused by environmental factors, especially caused by the effect of energy-rich radiation or by the action of toxic oxygen species, dry skin conditions, ageing of the skin or photosensitivity of the skin which manifest themselves as erythematous, inflammatory, allergic or autoimmune reactive symptoms. Furthermore, the invention relates to different galenic preparations which serve skin care from the cosmetic and/or dermatological viewpoint.

In galenic formulations, which are intended to protect against UV light, predominantly light absorbers are contained. In order to lessen the epidermal damage caused by the radiation, on the one hand substances are used which absorb the UV-B range of the sunlight between 280 and 320 nm. On the other hand, substances are incorporated which can absorb UV-A light in the range between 320 and 400 nm. Thus possible dermal damage which relates to the elastic fibres and the collagen stroma and the ageing of the skin visibly connected therewith, can be avoided. A further possible way of averting impairment from UV light, consists in the application of micronised particles (physical protection from light) which reflect the light on the skin surface.

The UV radiation leads to photochemical reactions, the photochemical reaction products, in particular toxic oxygen products, having a negative effect on the skin's metabolism. The toxic oxygen products derived from oxygen are for example energy-activated oxygen atoms. A representative of this reactive species is singlet oxygen which is considerably more reactive than the normal diradical triplet oxygen. Additional radical derivatives are superoxide anion and hydroxyl radical. As intermediates in the conversion of the superoxide anion into the hydroxyl radical, hydrogen peroxide occurs; in further reactions also harmful epoxides occur. These toxic oxygen species and the reaction products with the skin components also occur in the course of the normal metabolism to a limited extent. On exposure to energy-rich radiation, they are formed to an excess and are the cause of pathological skin conditions and accelerated skin ageing ("Skin Diseases Associated with Oxidative Injury". In "Oxidative Stress in Dermatology", Marcel Decker Inc. N.Y., Basle, Hong Kong ed. J. Fuchs and Lester Packer).

In order to neutralise toxic oxygen products formed and in order to control oxidation processes, substances are used which trap and extinguish radicals (radical scavengers) and/or which act as antioxidants. Such radical scavengers are described in great number in the literature. Often they are also described as primary antioxidants because they inhibit oxidative processes by terminating the radical chain reaction. The most well-known primary antioxidants used in topical formulations are for example sesamol, gallic acid, flavones or flavonoids (EP OS 595 694, DE 197 42 025A, DE 197 39 044, DE 196 51 428, DE OS 586 303 and EP OS 595 695). In DE 197 42 025A, flavones and flavonoids are quoted as active substances acting against the age-related cross-linking of dermal proteins which is seen as the cause of age spots.

What is disadvantageous about all these compounds is that they are either of synthetic origin or have to be extracted from plants and animals. They are not physiological in the concentration in which they are applied topically and in their application there is no guarantee that they will not be damaging to health, in particular in their long-term effect. Tocopherol or vitamin E (U.S. Pat. Nos. 4,144,325 and 4,248,861), which particularly inhibits the autooxidation of fats, occurs in human organisms. Since vitamin E is involved in a number of metabolic processes, an over-supply of same is not without risks.

Another substance which occurs in human organisms and can be manufactured by bioengineering with the aid of microorganisms, is hyaluronic acid. This is a particularly safe biopolymer which occurs in a mammal in a structure-forming manner in correspondingly large amounts. As a hydrocolloid it is in a position to bind a lot of water.

Hydrocolloid substances are used in preparations for external application in order to exploit the water-binding capacity of the compounds. In particular the highly biocompatible hyaluronic acid is present in many formulations as a water-binding substance. (U.S. Pat. Nos. 5,882,664, 5,391,373, 5,254,331, 5,087,446). In addition to tannins or catechins as oxygen radical scavengers to remove active oxygen and free radicals, hyaluronic acid is quoted in JP-9241637 in a formulation as a water-binding substance. In U.S. Pat. No. 5,571,503 hyaluronic acid is proposed besides esters of vitamin E, retinol and vitamin C in sun creams and in U.S. Pat. Nos. 5,886,142 and 5,942,245 in addition to antioxidants such as superoxide dismutase, cysteine and vitamin E to improve the hydration of the skin.

Hyaluronic acid is credited, in addition to its water-binding property, with properties of wound healing, encouraging the formation of vessels and improving penetration. In topical compositions according to DE 198 05 827A, hyaluronic acid effects protection of the skin against irritations. In U.S. Pat. No. 5,728,391, in an agent for treating skin disease, hyaluronic acid with a relative molar mass between 800 and 4,000 D is proposed.

In particular low-molecular hyaluronic acid fractions, which are produced for example from high-molecular hyaluronic acid of animal origin through splitting by means of ultrasound in the presence of hypochlorite (EP 0 944 007) have properties of healing wounds or encouraging the formation of vessels. In U.S. Pat. No. 4,303,676, hyaluronic acid mixtures are proposed between a hyaluronic acid fraction having relative molar masses of 10 to 200 kD and a second fraction with 1,000 and 4,5000 kD from cockscombs.

The object of the present invention therefore is to propose an agent for protecting the skin which in particular is biocompatible and is suitable for long-term application in human and veterinary medicine. The agent should be suitable for the treatment and/or the prophylaxis of traumatic symptoms and inflammations and ageing processes, due to environmental factors and/or as the consequence of other illnesses, including the effect of energy-rich radiation or of damage caused by the action of toxic oxygen products, without side effects occurring. Furthermore it is an object of the present invention that the agent can be used to care for or protect the skin from a cosmetic and/or dermatological viewpoint.

This object preferably is achieved according to the invention. Advantageous embodiments and developments of the invention will be apparent from the description of the invention provided herein.

Thus according to the invention, the agent for protecting the skin has a fragment mixture, produced by means of enzymes from hyaluronic acid, as well as pharmaceutical carriers and auxiliary substances known per se.

It is preferred here if a hyaluronate lyase which has been produced by microbial means is used.

The general term hyaluronidases describes three types of enzymes which act in differing manners to split hyaluronic acid [J. Ludowieg: The Mechanism of Hyaluronidases, JBC 236, 333–339 (1961)]. Firstly these are endohydrolases which split the β-(1–3) bonds by hydrolysis. These include the majority of the hyaluronidases from higher organisms, for example the hyaluronidase from bovine testes. These hyaluronate-glycan hydrolases (Enzyme class E.C. 3.2.1.35/36) split, in addition to hyaluronic acid bonds, also other glycosaminoglycans to a limited extent. Endo-β-hyaluronidase from blood gel, which splits the β-(1–4) bond in a highly specific manner, represents a further type. The third type of enzyme, hyaluronate lyase (Enzyme class: EC 4.2.2.1), splits the hyaluronic acid in the β-(1–4) bonds according to an elimination mechanism forming a double bond in (4–5) position on the glucuronic acid. For lyases, endo- and exo-splitting mechanisms are given in the literature.

The inventors were able to show that in particular in the preferred embodiment with the hyaluronate lyase unsaturated fragments are produced which obviously have excellent properties as a result of the final double bonds.

By preference the agent is produced by low-molecular unsaturated fragments, which are produced from high-molecular hyaluronic acid through the action of the enzyme hyaluronate lyase from a microorganism, preferably from a streptococcus, in particular from *streptococcus agalactiae* according to an elimination mechanism in an aqueous solution being introduced into the agent.

Surprisingly it has been shown that agents containing the unsaturated low-molecular hyaluronic acid fragments used according to the invention would have a better effect than an antioxidant as a radical scavenger, as an inhibitor preventing the formation of harmful photoproducts, as an agent against skin ageing, as protection against photoreactions and as an inhibitor of inflammatory reactions and general protection against toxic substances, than agents which contain the natural hyaluronic acid of animal or biotechnical hyaluronic acid or respectively their low-molecular saturated hydrolytic cleavage products according to prior art. This additional effect is obviously directly connected with the existence of the double bonds in the fragments produced according to the invention.

Other antioxidants and radical scavengers not based on hyaluronic acid may in partial regions of the listed effects act in the same way or better; however as frequently non-physiological active substances they do not have the high biocompatibility of the unsaturated hyaluronic acid fragments even at very high application doses. Furthermore the unsaturated fragments, analogously to the corresponding saturated hyaluronic acid fragments have the natural water retention capacity, the hydrocolloid character and the structure-giving properties of unsaturated fragments.

The agent according to the invention contains furthermore pharmaceutical carriers and/or further hydrophilic and/or lipophilic active substances and/or auxiliary substances. The high-molecular hyaluronic acid used as the initial substance can be produced by bioengineering or from animal tissue. In one embodiment, hyaluronate lyase immobilised to a solid carrier is used during elimination. The unsaturated low-molecular fragments according to the invention have relative molar masses of between 1 and 1500 kD, preferably between 10 and 300 kD. In the production of the formulations according to the invention, in one variant the low-molecular unsaturated fragment mixtures are incorporated in liquid form in concentrations of between 1.0 g/l and 500 g/l in amounts of 0.01 to 0.7 g per g formulation.

In another variant, the fragments are incorporated in solid form in amounts between 0.01 and 0.7 g per g formulation.

The formulation according to the invention is produced in the form of a paste, an ointment, a cream, an emulsion, a gel, a stick, a colloidal carrier system or a solution, preferably however as an o/w emulsion. It is advantageous that here the radical-binding active substance simultaneously has a high water-retention capacity corresponding to saturated hyaluronic acid.

In the agent can be contained pharmaceutical carriers and/or hydrophilic and/or lipophilic active substances and/or auxiliary substances. The fragment mixture and/or additional active substances and/or the auxiliary substances can be present incorporated into a colloidal carrier system, preferably in nanoparticles, liposomes or microemulsions.

As an auxiliary substance, a penetration modulator, for example urea can be present in amounts of 0.01 to 0.4 g per g formulation. The formulation according to the invention can furthermore contain other substances with radical scavenger properties, preferably vitamin E and vitamin C.

Without thereby limiting the invention to one manufacturing process, a typical manufacturing procedure for the low-molecular unsaturated fragments according to the invention will be represented by way of example. The enzyme used by preference, hyaluronate lyase, has, unlike other hyaluronate lyases of microbial origin, a relative molar mass of roughly 116 kD and an isoelectric point of pH 8.74 and acts as an endo-eliminase. The use of enzymes of animal origin expressly does not form part of the present invention, but is excluded for the present invention.

During the elimination reaction, the hyaluronic acid is present in an aqueous solution. The enzyme is added as an aqueous solution and the course of the reaction is followed with the aid of viscosity reduction or via other methods of determining the relative molar mass of the fragments. The reaction is terminated by heating to a temperature of 80° C. through denaturation of the enzyme. After prior separation of foreign substances containing protein, the fragments are produced as a solid substance from the batch through precipitation in ethanol or by freeze drying. In another type of embodiment, the enzyme is presented in a solid form immobilised on a carrier. Advantageous about the use of the carrier-immobilised form of the enzyme is that in the production of the fragments no enzyme remains in the reaction solution.

The invention is described in greater detail below through production examples, toxicity tests, assessments of the number of live cells after UV-irradiation as well as specific galenic formulations.

EXAMPLE 1

In order to produce the unsaturated low-molecular hyaluronic acid fragments according to an elimination mechanism, 0.5 g high-molecular hyaluronic acid produced by means of bioengineering and having an average relative molar mass of 1,800 kD is dissolved in 100 ml 0.05 M acetate buffer with an acidity of pH 7.0 within 12 hours under agitation at 37° C. Then the solution is incubated under agitation for 30 min with 10 000 IU hyaluronate lyase obtained from *streptococcus agalactiae*. After this time, the solution is heated to 85C. for 5 min and then quickly cooled to 20° C. The fragment mixture produced is then dialysed against distilled water. Thereafter there is lypophilic drying of the solution. The average relative molar mass of the fragment mixture is determined by means of viscometry. The fragments produced have an average relative molar mass of 150 kD.

EXAMPLE 2

The property of binding reducing radicals, is measured in cell-free systems with a lucigenin-reinforced xanthine oxidase test on the basis of the conversion of hypoxanthine to uric acid. The $O_2$-radicals produced in this process can be detected with lucigenin by relative chemiluminescence measurement. By the radical scavengers present, the $O_2$-radicals are neutralised and the chemiluminescence yield reduced. Allopurinol (Sigma chemicals Co) is used as standard, a substance which greatly inhibits the xanthine oxidase. An amount of 1 mg of the hyaluronic acid fragment according to the invention with a relative molar mass of 100 to 160 kD has a radical-binding activity which corresponds to that of 200 to 400 µg allopurinol. Hyaluronic acid with a relative molar mass of 1,800 kD has, on the other hand, a negligible radical-binding activity (Pierce, L. A., W. O. Tarnow-Mordi and I. A, Cree: Antibiotics Effects on Phagocyte Chemilunieszence in Vitro. In J. Clin. Lab. Res.- (1995) 25, 93–98).

Figure 1:
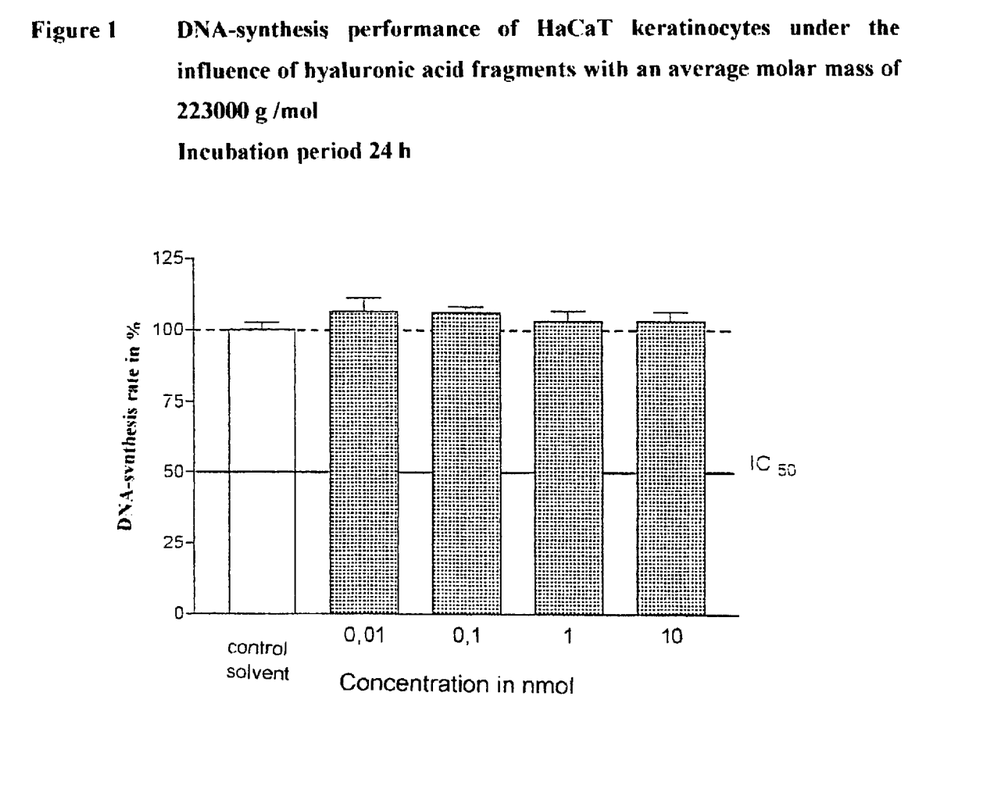
FIG. 1 illustrates DNA-synthesis performance of HaCaT keratinocytes under the influence of hyaluronic acid fragments with an average molar mass of 223000 g/mol (incubation period 24 h).
Figure 2:
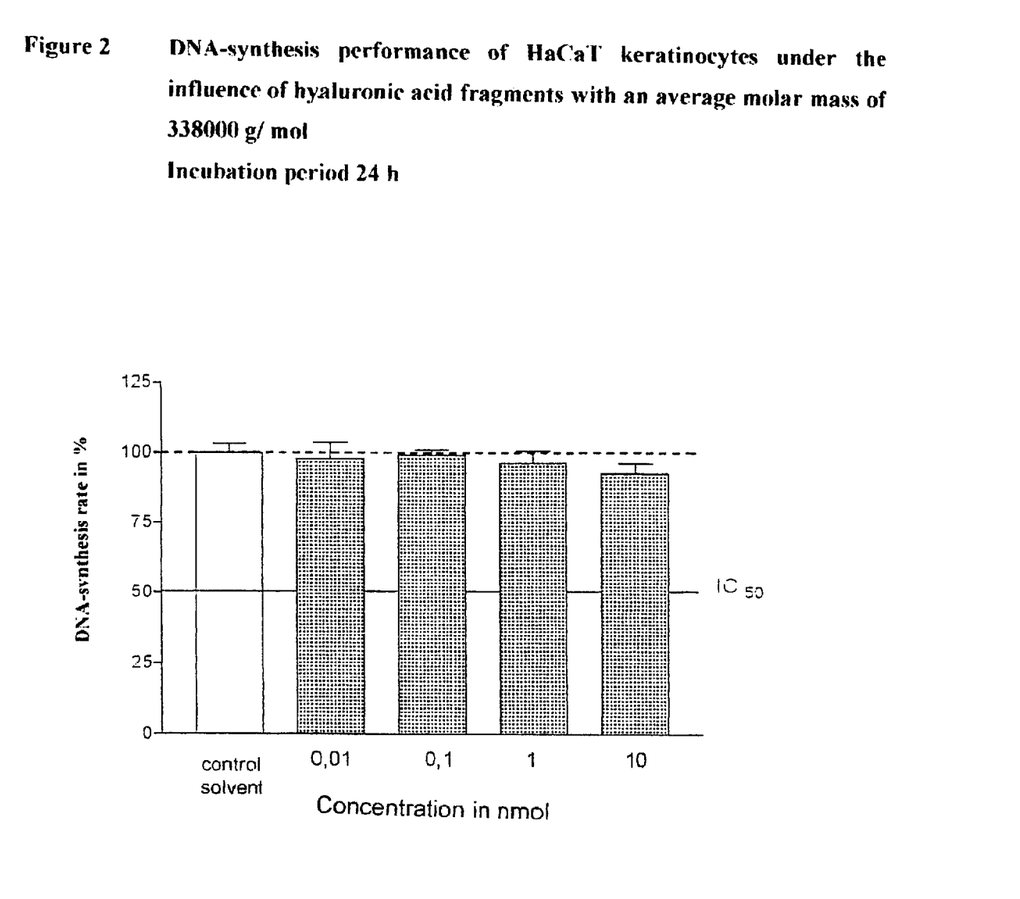
FIG. 2 illustrates DNA-synthesis performance of HaCaT keratinocytes under the influence of hyaluronic acid fragments with an average molar mass of 338000 g/mol (incubation period 24 h).
Figure 3:
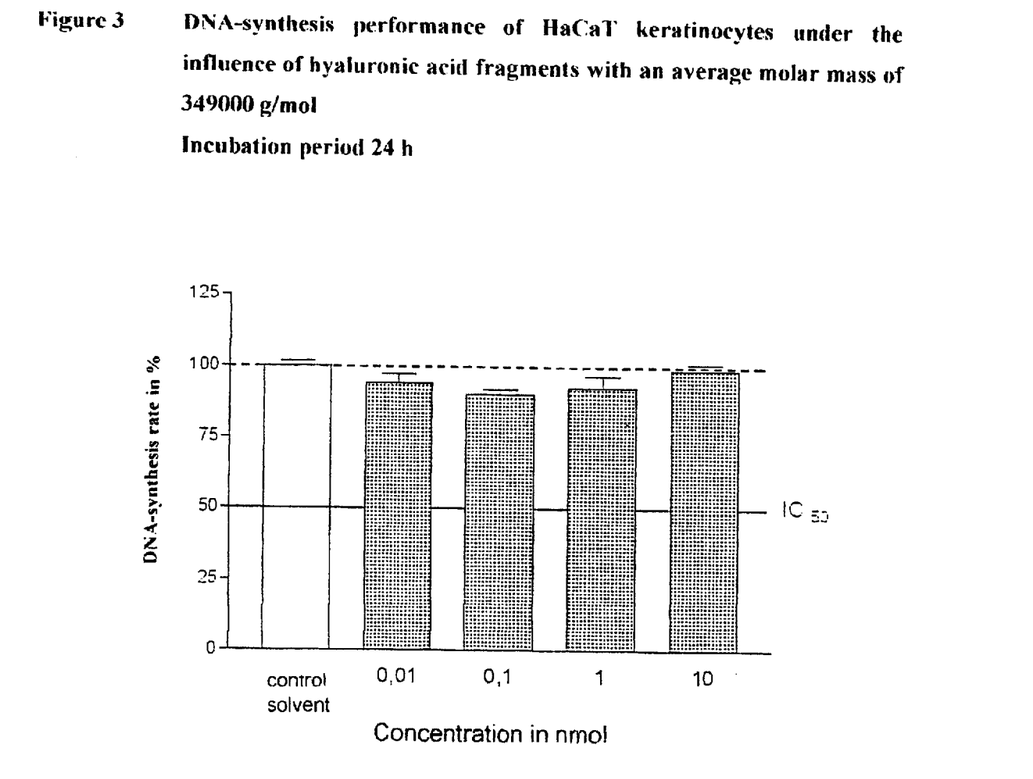
FIG. 3 illustrates DNA-synthesis performance of HaCaT keratinocytes under the influence of hyaluronic acid fragments with an average molar mass of 349000 g/mol (incubation period 24 h).
Figure 4:
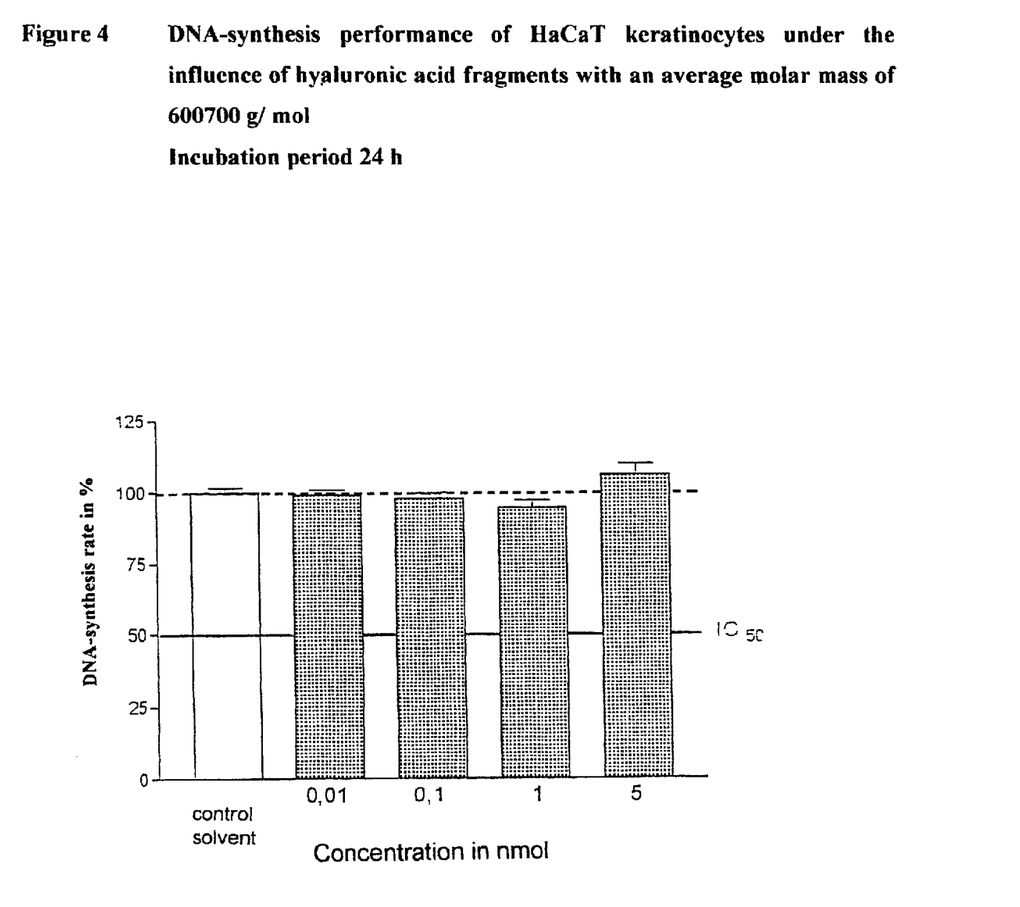
FIG. 4 illustrates DNA-synthesis performance of HaCaT keratinocytes under the influence of hyaluronic acid fragments with an average molar mass of 600700 g/mol (incubation period 24 h).
Figure 5:
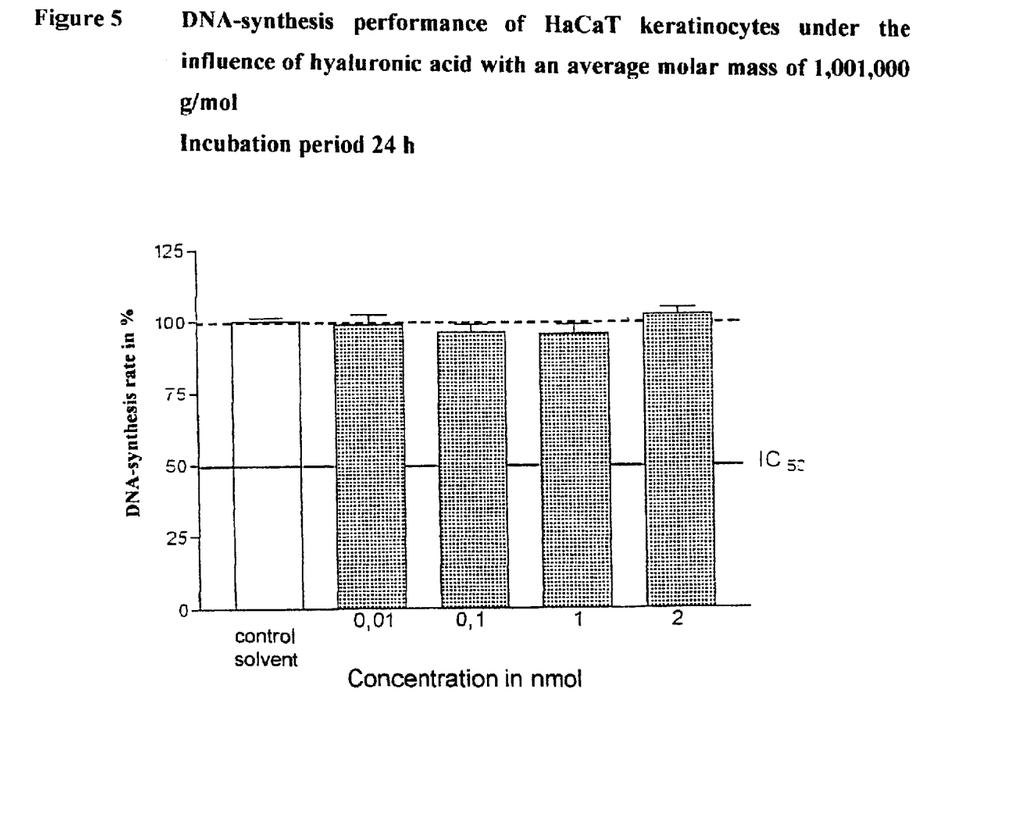
FIG. 5 illustrates DNA-synthesis performance of HaCaT keratinocytes under the influence of hyaluronic acid fragments with an average molar mass of 1,001,000 g/mol (incubation period 24 h).

Toxicity Tests on Human Keratinocytes
(FIGS. 1 to 5)

In order to characterise the influence of hyaluronic acid fragments of differing relative molar mass on the proliferation behaviour of human keratinocytes (HaCaT keratinocytes—made available by Prof. Dr. Norbert E. Fusenig: Deutsches Krebsforschungsinstitut Heidelberg, Germany), the DNA synthesis performance is determined with the aid of BrdU incorporation (Cell Proliferation ELISA, BrdU calorimetric—Boehringer Mannheim, Mannheim, Germany) into the DNA after a 24-hour period of incubation. For the following hyaluronic acid fragments examined, no toxic reaction of the cells could be observed. The results (FIGS. 1 to 5) indicate very good tolerance of the degraded molecules and also of the undigested hyaluronic acid.

Figure 6:
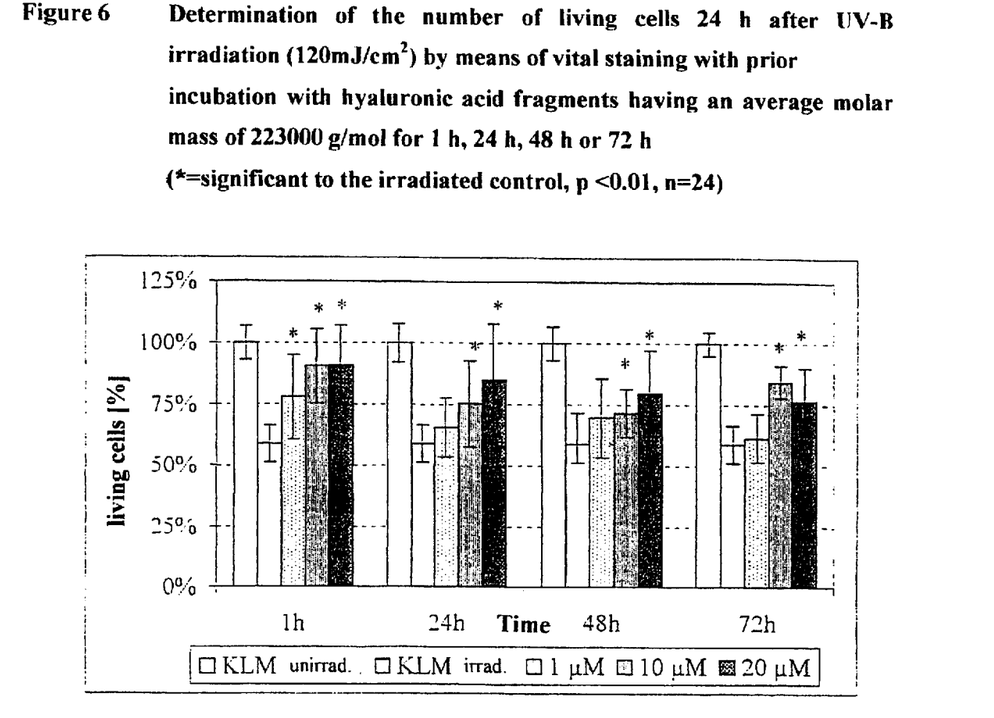
FIG. 6 illustrates the determination of the number of living cells 24 h after UV-B irradiation (120 mJ/cm$^2$) by means of vital staining with prior incubation with hyaluronic acid fragments having an average molar mass of 223000 g/mol for 1 h, 24 h, 48 h, or 72 h (*=significant to the irradiated control, p<0.01, n=24).
Figure 7:
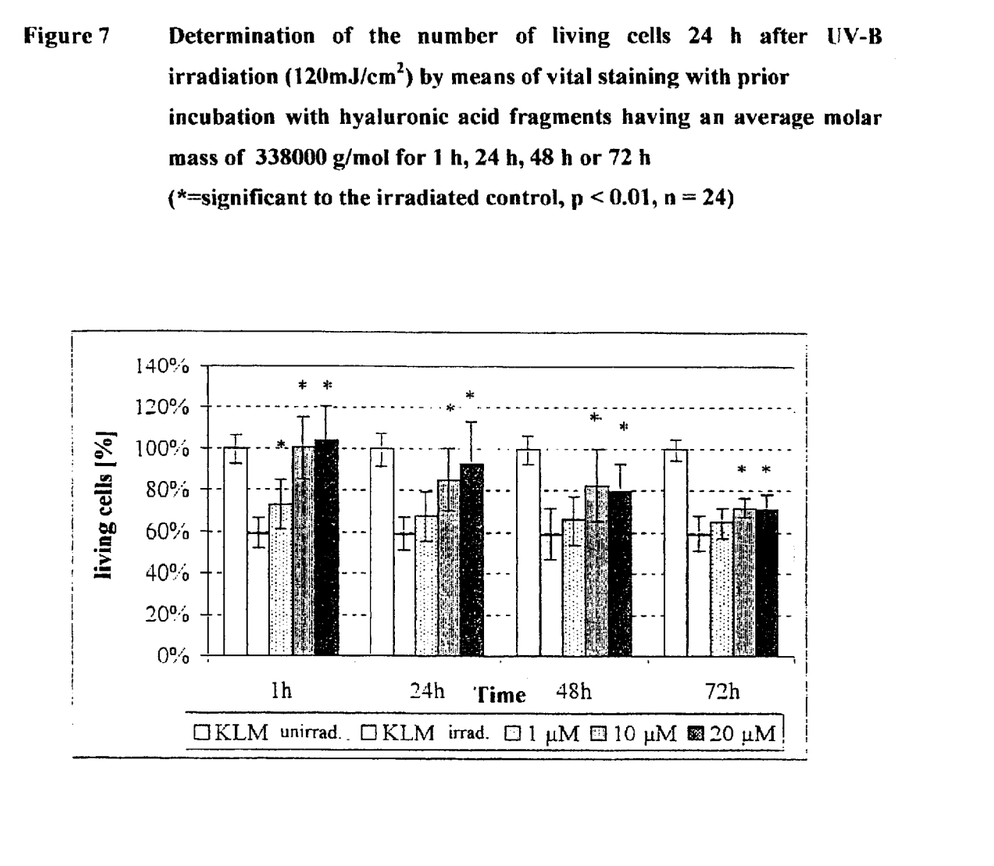
FIG. 7 illustrates the determination of the number of living cells 24 h after UV-B irradiation (120 mJ/cm$^2$) by means of vital staining with prior incubation with hyaluronic acid fragments having an average molar mass of 338000 g/mol for 1 h, 24 h, 48 h, or 72 h (*=significant to the irradiated control, p<0.01, n=24).
Figure 8:
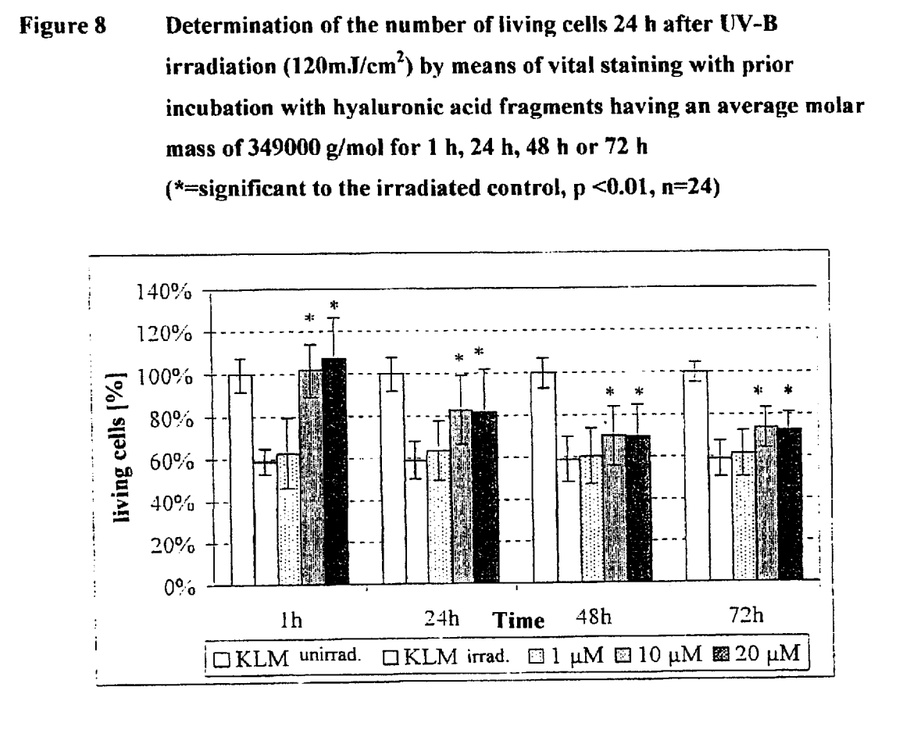
FIG. 8 illustrates the determination of the number of living cells 24 h after UV-B irradiation (120 mJ/cm$^2$) by means of vital staining with prior incubation with hyaluronic acid fragments having an average molar mass of 349000 g/mol for 1 h, 24 h, 48 h, or 72 h (*=significant to the irradiated control, p<0.01, n=24).
Figure 9:
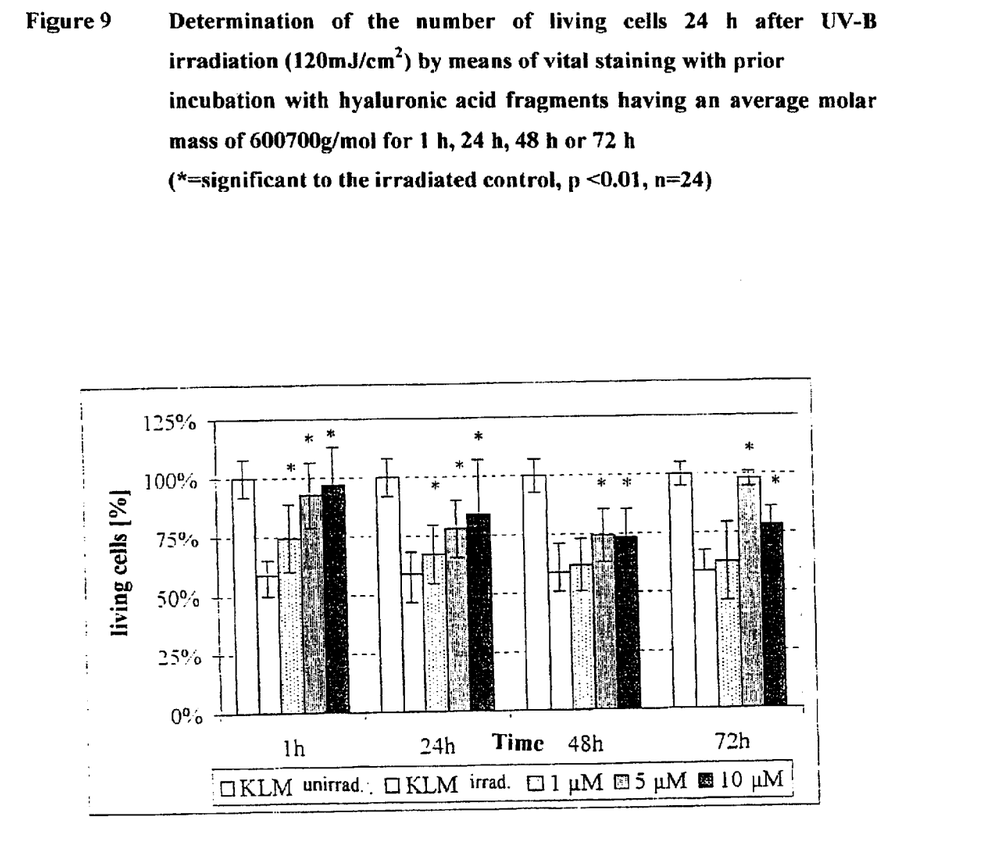
FIG. 9 illustrates the determination of the number of living cells 24 h after UV-B irradiation (120 mJ/cm$^2$) by means of vital staining with prior incubation with hyaluronic acid fragments having an average molar mass of 600700 g/mol for 1 h, 24 h, 48 h, or 72 h (*=significant to the irradiated control, p<0.01, n=24).
Figure 10:
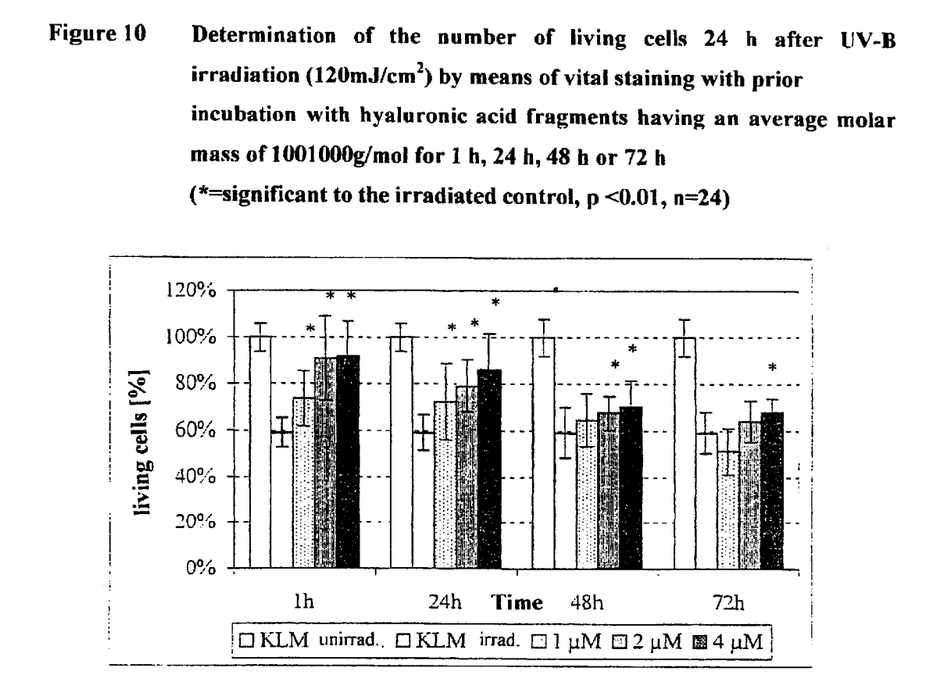
FIG. 10 illustrates the determination of the number of living cells 24 h after UV-B irradiation (120 mJ/cm$^2$) by means of vital staining with prior incubation with hyaluronic acid fragments having an average molar mass of 1001000 g/mol for 1 h, 24 h, 48 h, or 72 h (*=significant to the irradiated control, p<0.01, n=24).
Figure 11:
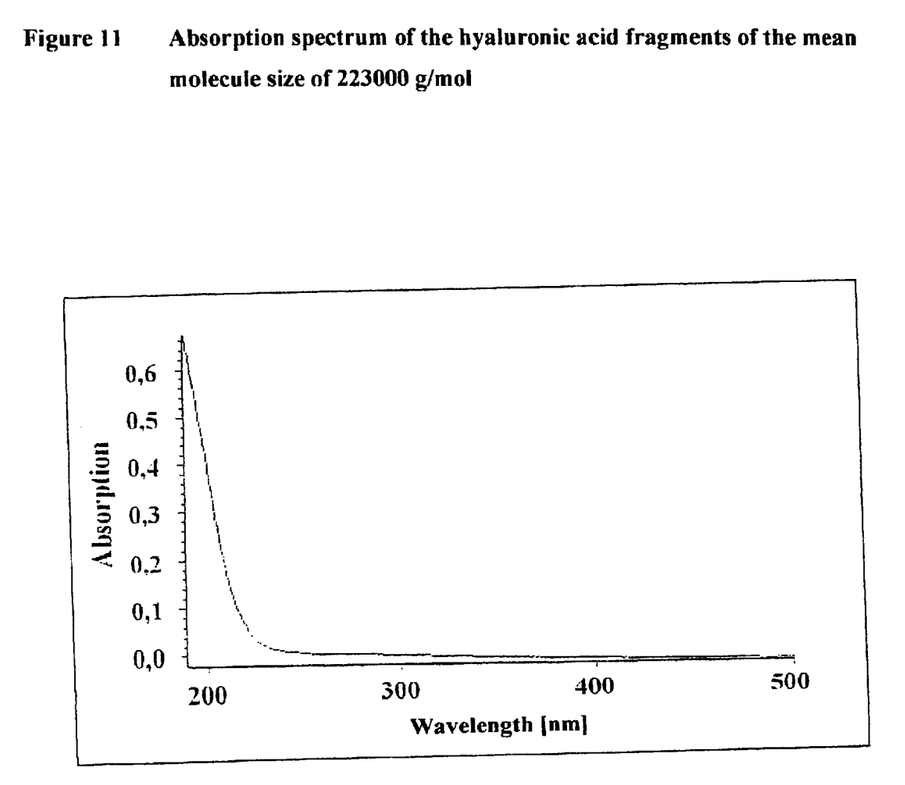
FIG. 11 illustrates the absorption spectrum of the hyaluronic acid fragments of the mean molecule size of 223000 g/mol.

Examples of the Protective Effect of Hyaluronic
Acid Fragments in Relation to UV-B Radiation
(FIGS. 6 to 11)

The hyaluronic acid fragments which showed no toxic influence on the HaCaT keratinocytes were investigated for their protective properties in relation to keratinocytes exposed to UV-B radiation. To this end, the corresponding cells were incubated in advance for respectively 1 h, 24 h, 48 h and 72 h with the respective fragment and then exposed to a radiation dose of 120 mJ/cm$^2$ (UV-B). This led to 50–60% damage of the irradiated control in comparison with the non-irradiated control. The vitality test to determine the number of living cells [SCHRODER, H et al., Naunyn-Schmiedeberg's Arch. Pharmacol. 347: 664–666 (1993)] always took place 24 h after the irradiation.

These results show protective effects of the hyaluronic acid fragments according to the invention in relation to the noxious UV-B, which can be taken in particular cases from the corresponding FIGS. 6 to 10.

For the effectiveness of the protection, the correlations of the period of pre-incubation and the concentration used, arising from the results can be derived. A filtering effect of the examined fragments can be excluded according to the absorption spectra present (see FIG. 11). Thus radical formation, produced by the irradiation with UV light, can be lessened by the presence of the hyaluronic acid fragments according to the invention.

Examples of Galenic Formulations in Which the
Hyaluronic Acid Fragments According to the
Invention Have Been Incorporated (Source for
Prescriptions)

Aqueous hydrophilic ointmeut (DAB)

| | |
|---|---|
| Hyaluronic acid fragment | 2.00% |
| Lanette ® N (emulsifying cetyl stearyl alcohol DAB 10) | 9.00% |
| Paraffinum subliquidum (viscous paraffin) | 10.50% |
| Vaselinum album (white Vaseline) | 10.50% |
| Aqua bidestillata | ad 100.00% |

-continued

Aqueous wool alcohol ointment (DAB)

| | | |
|---|---|---|
| Hyaluronic acid fragment | | 2.00% |
| Alcoholes lanae (wool alcohols) | | 3.00% |
| Alcohol cetystearylicus (cetyl stearyl alcohol) | | 0.25% |
| Vaselinum album (white Vaseline) | | 46.75% |
| Aqua bidestillata | ad | 100.00% |

O/W Emulsion

| | | |
|---|---|---|
| Cetyl stearate/PEG 100 stearate | | 3.00% |
| Cetyl stearyl alcohol 20 EO | | 1.00% |
| Cetyl stearyl alcohol | | 1.15% |
| Polydimethyl silicone 100 | | 1.00% |
| Caprylic/capric acid triglyceride | | 4.00% |
| Dioctyl ether | | 5.00% |
| 4-methoxy-cinnamic acid-2-ethylhexyl ester | | 3.00% |
| 4-methoxy-cinnamic acid-isoamyl ester | | 3.00% |
| Glycerol | | 3.00% |
| Magnesium aluminium silicate | | 1.00% |
| Zinc oil | | 5.00% |
| Hyaluronic acid fragment | | 2.00% |
| Aqua bidestillata | ad | 100.00% |

Unguentum emulsificans aquosum (SR)

| | | |
|---|---|---|
| Alcoholes emulsificans | | 21.00% |
| Cera perliquida | | 10.00% |
| Glycerolum | | 5.00% |
| Propylium hydroxybenzoicum | | 0.06% |
| Methylium hydroxybenzoicum | | 0.14% |
| Ethanolum (90 Vol-%) | | 1.80% |
| Hyaluronic acid fragment | | 2.00% |
| Aqua bidestillata | ad | 100.00% |

Hydrogel

| | | |
|---|---|---|
| 4-methoxy-cinnamic acid-2-ethylhexyl ester | | 3.50% |
| 1-(4-tert.-butyl phenyl)-3-(4'methoxyphenyl)-propane-1,3-dione | | 1.00% |
| Tocopherol acetate | | 1.00% |
| Hyaluronic acid fragment | | 2.00% |
| Acrylate copolymer Carboset 514 | | 10.00% |
| Ethanol | ad | 100.00% |

Base cream DAC

| | | |
|---|---|---|
| Glycerol monostearate 60 | | 4.00% |
| Cetyl alcohol | | 6.00% |
| Medium chain triglycerides | | 7.50% |
| White Vaseline | | 25.50% |
| Macrogol-100-glycerol monostearate | | 7.00% |
| Propylene glycol | | 10.00% |
| Tocopherol acetate | | 2.00% |
| Hyaluronic acid fragment | | 2.00% |
| Water | ad | 100.00% |

(NRF)

| | | |
|---|---|---|
| Sorbitan monostearate 60 | | 2.00% |
| Macrogol stearate 400 | | 3.00% |
| Glycerol 85% | | 5.00% |
| Medium chain triglycerides | | 5.00% |
| Anhydrous citric acid | | 0.07% |
| Potassium sorbate | | 0.14% |
| Tocopherol acetate | | 0.50% |
| Hyaluronic acid fragment | | 1.00% |
| Water | ad | 100.00% |

What is claimed is:

1. A composition for protecting and maintaining, or for reconstructing, the normal function and structure of the human or animal skin and/or mucosa and for preventing skin damage caused by environmental factors including UV, comprising low molecular weight unsaturated hyaluronic acid fragments produced by enzymatic reaction of a high molecular weight hyaluronic acid with a microbial hyaluronate lyase of the enzyme class E.C. 4.2.2.1, as well as pharmaceutical carriers and/or hydrophilic and/or lipophilic active substances and/or auxiliary substances.

2. The composition according to claim 1, wherein the low molecular weight unsaturated hyaluronic acid fragments are produced by partial digestion of the high molecular weight hyaluronic acid with the microbial hyaluronate lyase in an aqueous solution.

3. The composition according to claim 2, wherein the low molecular weight unsaturated hyaluronic acid fragments are produced by partial digestion of the high molecular weight hyaluronic acid with the microbial hyaluronate lyase in a carrier-immobilized form.

4. The composition according to claim 1, wherein, the low molecular weight unsaturated hyaluronic acid fragments are produced by partial digestion of the high molecular weight hyaluronic acid with a hyaluronate lyase obtained from *streptococcus agalactiae*.

5. The composition according to claim 4, wherein the hyaluronate lyase obtained from *streptococcus agalactiae* has a relative molar mass in the region of 116,000 D and anisoelectric point in the region of IP 8.6.

6. The composition according to claim 1, wherein the low molecular weight unsaturated hyaluronic acid fragments have an average relative molar mass between 1,000 and 1,500,000 D.

7. The composition according to claim 1, wherein the low molecular weight unsaturated hyaluronic acid fragments are mixed into the composition in liquid form with concentrations of 1.0 g/l to 500 g/l in amounts of 0.01 to 0.7 g per g composition.

8. The composition according to claim 1, wherein the low molecular weight unsaturated hyaluronic acid fragments are mixed into the composition in solid form in amounts of 0.01 to 0.7 g per g composition.

9. The composition according to claim 1, wherein the composition is in the form of a paste, ointment, cream, emulsion, gel, or stick.

10. The composition according to claim 1, wherein the low molecular weight unsaturated hyaluronic acid fragments and/or the active substances and/or the auxiliary substances are incorporated in a colloidal carrier system.

11. The composition according to claim 1, wherein penetration modulators are used as an auxiliary substance.

12. The composition according to claim 11, wherein urea is used as the penetration modulator in the concentration range of 0.01 to 0.4 g urea per g composition.

13. The composition according to claim 1, further comprising a substance having radical scavenger properties.

14. The composition according to claim 6, wherein the low molecular weight unsaturated hyaluronic acid fragments have an average relative molar mass between 10,000 and 300,000 D.

15. The composition according to claim 9, wherein the composition is in the form of an o/w emulsion.

16. The composition according to claim 10, wherein the colloidal carrier system is selected from nanoparticles, liposomes, and microemulsions.

17. The composition according to claim 13, wherein the substance having radical scavenger properties is selected from vitamin E and vitamin C.

* * * * *